United States Patent
Muraki

(10) Patent No.: US 8,482,731 B2
(45) Date of Patent: Jul. 9, 2013

(54) MICROPARTICLE MEASURING APPARATUS

(75) Inventor: Yosuke Muraki, Toyko (JP)

(73) Assignee: Felica Networks, Inc., Tokyo (JP)

( * ) Notice: Subject to any disclaimer, the term of this patent is extended or adjusted under 35 U.S.C. 154(b) by 462 days.

(21) Appl. No.: 12/792,859

(22) Filed: Jun. 3, 2010

(65) Prior Publication Data

US 2010/0315639 A1 Dec. 16, 2010

(30) Foreign Application Priority Data

Jun. 10, 2009 (JP) ................................ P2009-138789

(51) Int. Cl.
*G01N 21/00* (2006.01)

(52) U.S. Cl.
USPC .......... 356/342; 356/335; 356/336; 356/338; 250/459.1

(58) Field of Classification Search
USPC ................ 356/342, 335, 336, 339; 250/459.1
See application file for complete search history.

(56) References Cited

U.S. PATENT DOCUMENTS

| | | | | |
|---|---|---|---|---|
| 5,528,045 A | * | 6/1996 | Hoffman et al. | 250/458.1 |
| 5,594,544 A | * | 1/1997 | Horiuchi et al. | 356/73 |
| 5,948,684 A | * | 9/1999 | Weigl et al. | 436/52 |
| 6,317,511 B1 | * | 11/2001 | Horiuchi | 382/133 |
| 7,688,427 B2 | * | 3/2010 | Cox et al. | 356/39 |
| 2009/0103091 A1 | * | 4/2009 | Jones et al. | 356/342 |

FOREIGN PATENT DOCUMENTS

| | | |
|---|---|---|
| JP | 9-196916 | 7/1997 |
| JP | 11-83724 | 3/1999 |
| JP | 2003-107099 | 4/2003 |
| JP | 2007-46947 | 2/2007 |

\* cited by examiner

*Primary Examiner* — Tarifur Chowdhury
*Assistant Examiner* — Isiaka Akanbi
(74) *Attorney, Agent, or Firm* — K&L Gates LLP

(57) ABSTRACT

A microparticle measuring apparatus which includes a flow channel through which a solution containing microparticles flows, an optical detecting unit configured to direct a laser beam to microparticles passing through the flow channel and detecting light for measurement emanating from the microparticles and converting the thus detected light into electrical signals, a solution feeding unit configured to feed the flow channel with either a sample solution containing microparticles of interest or a calibration solution containing reference microparticles that exhibit uniform optical characteristics, and an optical axis correcting unit configured to optimize the relative position of the flow channel with respect to the laser beam in response to the intensity of electrical signals from the reference microparticles.

7 Claims, 3 Drawing Sheets

MICROPARTICLE MEASURING APPARATUS

CROSS REFERENCES TO RELATED APPLICATIONS

The present application claims priority to Japanese Priority Patent Application JP 2009-138789 filed in the Japan Patent Office on Jun. 10, 2009, the entire content of which is hereby incorporated by reference.

BACKGROUND

The present application relates to a microparticle measuring apparatus and, more particularly, to a microparticle measuring apparatus capable of highly accurate measurement which has its optical axis corrected at arbitrary or prescribed timing during measurement.

There has been an apparatus used to optically identify the characteristic properties of such microparticles as those associated with living bodies (e.g., cells, microorganism and liposomes) and with industries (e.g., latex particles, gel particles, and synthetic particles). It is so designed as to introduce a dispersion of microparticles into a flow channel and direct a light beam to the microparticles passing through the flow channel.

Most popular among apparatuses to measure microparticles associated with living bodies is one for flow cytometry, which is called flow cytometer. (See "Saibou Kougaku (Cell Engineering), supplement volume, Experiment Protocol Series, Mastering of Flow Cytometry," by H. Nakauchi, issued by Shuujunsha, 2nd edition, issued Aug. 31, 2006.) One type of it is intended only to identify the characteristic properties of microparticles and the other is so designed as to fractionate microparticles with desired properties according to the results of measurement obtained by the first type. The latter, which is used to fractionate cells, is referred to as "cell sorter."

The existing flow cytometer is so designed as to determine the characteristic properties (e.g., size and structure) of such microparticles as cells and microbeads in the following manner. A sample solution containing microparticles of interest is introduced into the center of the laminar flow of a sheath solution passing through a flow cell, so that the microparticles are lined up in the flow cell. The microparticles passing in a line through the flow cell are illuminated with a laser beam, and the scattered light or fluorescent light emanating from them is detected for determination of their characteristic properties. The system for directing a laser beam to the sample flow in the optical detection unit is divided into "closed system" (which is designed such that illumination with a laser beam is accomplished in the flow cell) and "jet-in-air system" (which is designed such that a laser beam is directed to the jet water column discharged from a jet nozzle). The foregoing step may optionally be followed by fractionation of microparticles having desired characteristic properties in such a way that the sample solution containing microparticles is discharged in the form of droplets from the flow cell and individual droplets are moved in different controlled directions.

Japanese Patent Laid-open No. 2007-46947 discloses a existing cell sorter (as shown in its FIG. 7) which is composed of a flow cell having a flow channel that causes cells (dyed with a fluorescent labeling reagent) to be lined up therein, an optical system that illuminates the cells with a laser beam and detects scattered light or fluorescent light, and a cell fractionating system that controls the moving direction of droplets discharged out of the flow cell. This cell sorter is provided with the optical detection unit of closed system.

For the optical detection unit to be capable of efficient detection of scattered light or fluorescence emanated from microparticles, it needs adjustment for the laser beam to orthogonally intersect with and focus on the sample flow. This step is usually called optical axis correction or "calibration." The optical axis correction is accomplished by flowing microbeads for calibration and adjusting the position and focus of the condenser lens while watching the histogram data of such microbeads. In this way the relative position of the laser beam, the sample flow, and the detector is optimized. Japanese Patent Laid-open No. Hei 11-83724 and Japanese Patent Laid-open No. Hei 9-196916 disclose the microbeads for calibration used for the optical axis correction.

In the meantime, there has recently been developed a microchip which is composed of a silicon or glass substrate and a region or flow channel formed therein in which chemical or biological analysis is carried out. The analytical system using such a microchip is referred to as µ-TAS (micro-total-analysis system) or lab-on-chip or biochip.

The µ-TAS may be applied to the technology for fractionation of microparticles which examines microparticles for their characteristic properties by optical, electrical, or magnetic device while they are passing through the flow channel or region formed in the microchip. For example, Japanese Patent Laid-open No. 2003-107099 discloses a microchip for microparticles separation which is composed of a substrate and those components formed therein as listed below. A flow channel for introduction of a solution containing microparticles. A flow channel to form a sheath flow therein which is arranged along at least one side of said first flow channel. A microparticle measuring unit to measure the thus introduced microparticles. Two or more microparticle fractionating flow channels to fractionate and recover microparticles which are arranged downstream said microparticle measuring unit. The foregoing microchip has an electrode near the entrance of the microparticle fractionating flow channel from the microparticle measuring unit. The microparticle fractionating apparatus provided with this microchip is able to control the direction of movement of microparticles by mutual action between the electric field of the electrode and the microparticles, thereby fractionating microparticles.

The flow cytometer (of microchip type) based on µ-TAS may have the flow channel formed in a disposable microchip so as to prevent cross-contamination of samples during measurement.

SUMMARY

The flow cytometer with the closed system has the flow cell accurately positioned and rarely allows relative displacement of the laser beam, sample flow channel, and detector; therefore, it demands the optical axis correction only once after several measurements. On the other hand, the flow cytometer with the jet-in-air system needs operation to detach the jet nozzle and clean it of sample causing clogging. This operation changes the position of the jet water column, and hence the optical axis correction is necessary each time of measurement. Also, the flow cytometer of microchip type needs the optical axis correction each time of chip exchange because the chip mounting position changes when the microchip is exchanged.

However, even though the optical axis correction is carried out as mentioned above, the corrected optical axis sometimes gets out of position during actual measurement because the apparatus undergoes vibration, the sheath flow changes in pressure, the apparatus changes in temperature, the sample flow channel in the flow cell changes in position, and the jet water column changes in position. This is true particularly in the case of flow cytometer of microchip type, because the microchip made of plastics is easily affected by temperature change due to laser irradiation and the sample flow in the flow channel gets out of position. The displacement of the optical axis that occurs during measurement due to vibration and change in pressure and temperature decreases the accuracies of measurement and even disables measurement.

Thus, in an embodiment of the present application provides a microparticle measuring apparatus which is capable of automatically correcting the displacement of the optical axis that occurs during measurement, thereby allowing highly accurate measurement.

According to embodiment, the above-mentioned embodiment is achieved by a microparticle measuring apparatus which includes a flow channel through which a solution containing microparticles flows, optical detecting means for directing a laser beam to microparticles passing through the flow channel and detecting light for measurement emanating from the microparticles and converting the thus detected light into electrical signals, solution feeding means for feeding the flow channel with either a sample solution containing microparticles of interest or a calibration solution containing reference microparticles that exhibit uniform optical characteristics, and optical axis correcting means for optimizing the relative position of the flow channel with respect to the laser beam in response to the intensity of electrical signals from the reference microparticles.

The microparticle measuring apparatus mentioned above may be modified such that the optical axis correcting means moves and optimizes the relative position in the incident direction of the laser beam and/or in the direction perpendicular to the plane containing the direction and the flowing direction of the flow channel, so that the intensity of electrical signals emanated from the reference microparticles reaches a prescribed value.

The microparticle measuring apparatus mentioned above may be further modified such that the solution feeding means feeds the flow channel with either the sample solution or the calibration solution alternately and the optical axis correcting means optimizes the relative position while the sample solution is flowing to the flow channel in response to the intensity of electrical signals emanated from the reference microparticles which was previously measured while the calibration solution was flowing to the flow channel.

The microparticle measuring apparatus mentioned above may additionally have an acceleration sensor to detect vibration of the apparatus proper. In this case, it may be modified such that the solution feeding means feeds the flow channel with the calibration solution for a prescribed period of time in response to the output of detected signals from the acceleration sensor.

The microparticle measuring apparatus mentioned above may be constructed such that the flow channel is formed in a microchip and provided with a temperature sensor to measure the temperature of the microchip. In this case, it may be modified such that the solution feeding means feeds the flow channel with the calibration solution for a prescribed period of time when the value measured by the temperature sensor exceeds a prescribed value.

The term "microparticles" as used in an embodiment embraces any microparticles associated with living bodies, such as cells, microorganisms, and liposomes, and any synthetic microparticles for industrial use, such as latex particles and gel particles.

Microparticles associated with living bodies include chromosomes in various cells, liposomes, mitochondria, and organelles. The cells include animal cells (such as blood cells) and vegetable cells. The microorganisms include bacteria such as *Escherichia coli*, viruses such as tobacco mosaic virus, and fungi such as yeast. They also include polymers such as nucleic acids, proteins, and complexes thereof. Microparticles for industrial use include those of organic or inorganic polymeric material and metallic material. The organic material includes polystyrene, styrene-divinylbenzene, and polymethyl methacrylate. The inorganic polymeric material includes glass, silica, and ceramics. The metallic material includes gold colloid and alumina. These microparticles are usually spherical but may be aspherical in some cases. They are not specifically restricted in size and mass.

In addition, the term "reference microparticles" as used in the present embodiment denotes an aggregate of microparticles which, when measured under a prescribed condition, is used to optimize the relative position of the laser beam, the sample flow, and the detector, and the ratio of amplification of the optical amplifier. The reference microparticles widely embrace any microparticles for calibration used to correct the optical axis in flow cytometer. They include immobilized microparticles associated with living bodies and such synthetic particles as disclosed in Patent Documents 2 and 3 mentioned above.

The present embodiment provides a microparticle measuring apparatus which is capable of highly accurate measurement because it is so designed as to automatically correct the displacement of the optical axis that occurs during measurement.

Additional features and advantages are described herein, and will be apparent from the following Detailed Description and the figures.

DETAILED DESCRIPTION

The present application is described below in greater detail with reference to the drawings according to an embodiment.
1. Construction of the microparticle measuring apparatus
  (1) Microchip
  (2) Optical detecting unit
  (3) Solution feeding unit
  (4) Optical axis correcting unit
  (5) Acceleration sensor and temperature sensor
  (6) General control unit
2. Action of the microparticle measuring apparatus
  (1) Step S1 (Measurement of microparticles under test)
  (2) Step S2 (Switching to calibration solution)
  (3) Step S3 (Measurement of reference microparticles)
  (4) Step S4 (Correction of optical axis)
  (5) Step S5 (Switching to sample solution)
  (6) Step S6 (Resumption of measurement of microparticles under test)
  (7) Timing of Step S2
1. Construction of the Microparticle Measuring Apparatus FIG. 1 is a schematic diagram illustrating the construction of the microparticle measuring apparatus according to the present embodiment.

(1) Microchip

Figure 1:
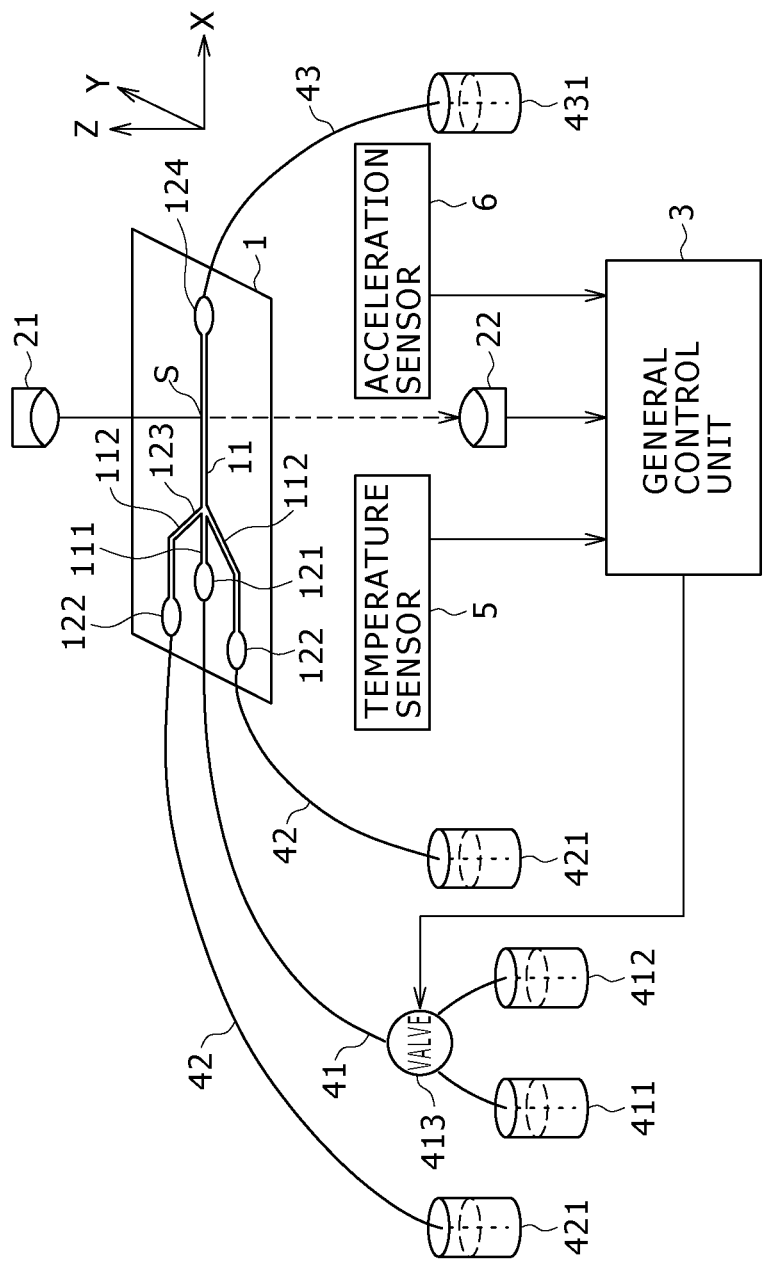
FIG. 1 is a schematic diagram illustrating the construction of the microparticle measuring apparatus according an embodiment.

There is shown in FIG. 1 the microchip 1. The microchip 1 has the flow channel 11 formed therein, which receives a sample solution containing microparticles of interest or a calibration solution containing reference microparticles and also functions as a site for measurement of optical characteristics of microparticles passing through it. In what follows, the term "sample solution and the like" will be occasionally used to denote the sample solution and calibration solution altogether, and the term "microparticles under test and the like" will be used to denote the microparticles under test and reference microparticles altogether.

There is also shown the sample solution inlet 121, which introduces the sample solution or calibration solution into the branched flow channel 111. The thus introduced sample solution or calibration solution joins at the meeting point 123 the sheath solution which has been introduced from the sheath solution inlets 122 and 122 into the branched flow channels 112 and 112. At this time, the sample solution and the like being fed from the branched flow channel 111 forms a laminar flow, which is held between laminar flows of the sheath solution being fed from the inlets 122 and 122 in such a way that the microparticles in the sample solution and the like are lined up in the laminar flow during their passage through the flow channel 11.

The microchip 1 is formed from glass or various plastics (such as PP, PC, COP, and PDMS). A suitable material should be selected which is transparent to the illuminating light from the optical detecting units 21 and 22 (mentioned later), has a low level of self fluorescence emission, and has a low level of chromatic dispersion which is desirable for limited optical errors.

The flow channel 11 etc. in the microchip 1 may be formed by wet etching or dry etching performed on a glass substrate. They may also be formed by nanoimprinting on a plastic substrate or by injection molding and machining. The microchip 1 may be formed by sealing the substrate (on which the flow channel 11 etc. have been formed) with any material which is identical with or different from the substrate.

(2) Optical Detecting Unit

The microparticles passing through the flow channel 11 are examined for optical characteristics by the paired optical detecting units 21 and 22 shown in FIG. 1. The optical detecting unit 21 directs a laser beam (measuring light) toward the microparticles passing through the flow channel 11 at a specific position and the optical detecting unit 22 receives light (to be measured) emanating from the microparticles and converts the received light into electrical signals. That site of the microchip to which the laser beam is directed from the optical detecting unit 21 will be referred to as "illuminating site S" hereinafter. Incidentally, the flow channels for sample solution and sheath solution in the microparticle measuring apparatus are not restricted to those mentioned above so long as they allow microparticles to line up in the laminar flow of the sample solution and feed the sample solution to the illuminating site S. Incidentally, the foregoing description assumes that the flow channel 11 formed in the microchip functions as the optical detecting part where the microparticles are examined for optical characteristics. However, the microparticle measuring apparatus may have the optical detecting part which is based on the existing closed system or jet-in-air system. The flow channel 11 corresponds to the flow channel in the flow cell (in the former case) or the jet water column discharged from the jet nozzle (in the latter case).

The optical detecting units 21 and 22 may have the same structure as those in the existing flow cytometer. To be specific, the optical detecting unit 21 is an illuminator composed of a laser light source, a condenser lens to direct the laser beam to microparticles, a dichroic mirror, and a bandpass filter. The optical detecting unit 22 is a detector to detect light emanating from microparticles illuminated by the laser beam. The detector is composed of a PMT (photo multiplier tube) or an areal imaging device such as CCD (Charge Coupled Device) and CMOS (Complementary Metal Oxide Semiconductor) elements. Incidentally, the illustrated one is composed of separate illuminating and detecting systems. However, they may be combined into one system.

The light detecting unit 22 detects light emanating from the microparticles being illuminated by the laser beam. The light for detection may be fluorescent light or scattered light due to forward scattering, side scattering, Rayleigh scattering, and Mie scattering. The detected light is subsequently converted into electrical signals to be sent to the general control unit 3. Using the electrical signals, the general control unit 3 determines the characteristic properties of the microparticles. The general control unit 3 also sends signals to the optical axis correcting unit (mentioned later) in response to the intensity of electrical signals resulting from the reference microparticles, so that the optical axis correcting unit optimizes the relative position of the flow channel 11 with respect to the laser beam emanating from the optical detecting unit 21.

Incidentally, the optical detecting units 21 and 22 in the microparticle measuring apparatus may be replaced by any electrical or magnetic detecting unit. In this case, the flow channel 11 is flanked with minute electrodes facing each other which measure changes in resistance, capacitance, inductance, impedance, electric field, magnetic field, or magnetization between them.

(3) Solution Feeding Unit

There is shown in FIG. 1 the solution feeding unit 41 which introduces the sample solution or calibration solution into the sample solution inlet 121. There are also shown the sample solution reservoir 411 to store the sample solution and the calibration solution reservoir 412 to store the calibration solution. The sample solution feeding unit 41 has a feeding pump of ordinary type, and it feeds the sample solution or calibration solution to the sample solution inlet 121 according as the valve 413 is switched. The valve 413 receives signals from the general control unit 3, and the solution feeding unit 41 switches the valve 413 according to the signals to feed either the sample solution or the calibration solution to the sample solution inlet 121.

There is shown in FIG. 1 the sheath solution feeding units 42 and 42 which introduce the sheath solution into the sheath solution inlets 122 and 122. There is also shown the sheath solution reservoirs 421 and 421 to store the sheath solution. There is also shown the waste tank 431 (placed outside the microchip 1 and connected to the discharging unit 43) which receives from the outlet 124 the sample solution and the like and the sheath solution which have been introduced into the flow channel 11 and have passed through the illuminating site S. The sheath solution feeding unit 42 and discharging unit 43 may be composed of ordinary pumps for solution delivery.

(4) Optical Axis Correcting Unit

The microparticle measuring apparatus has an optical axis correcting unit (not shown). The optical axis correcting unit moves the relative position of the flow channel 11 with respect to the laser beam emanating from the optical detecting unit 21 (for illumination).

Figure 2:
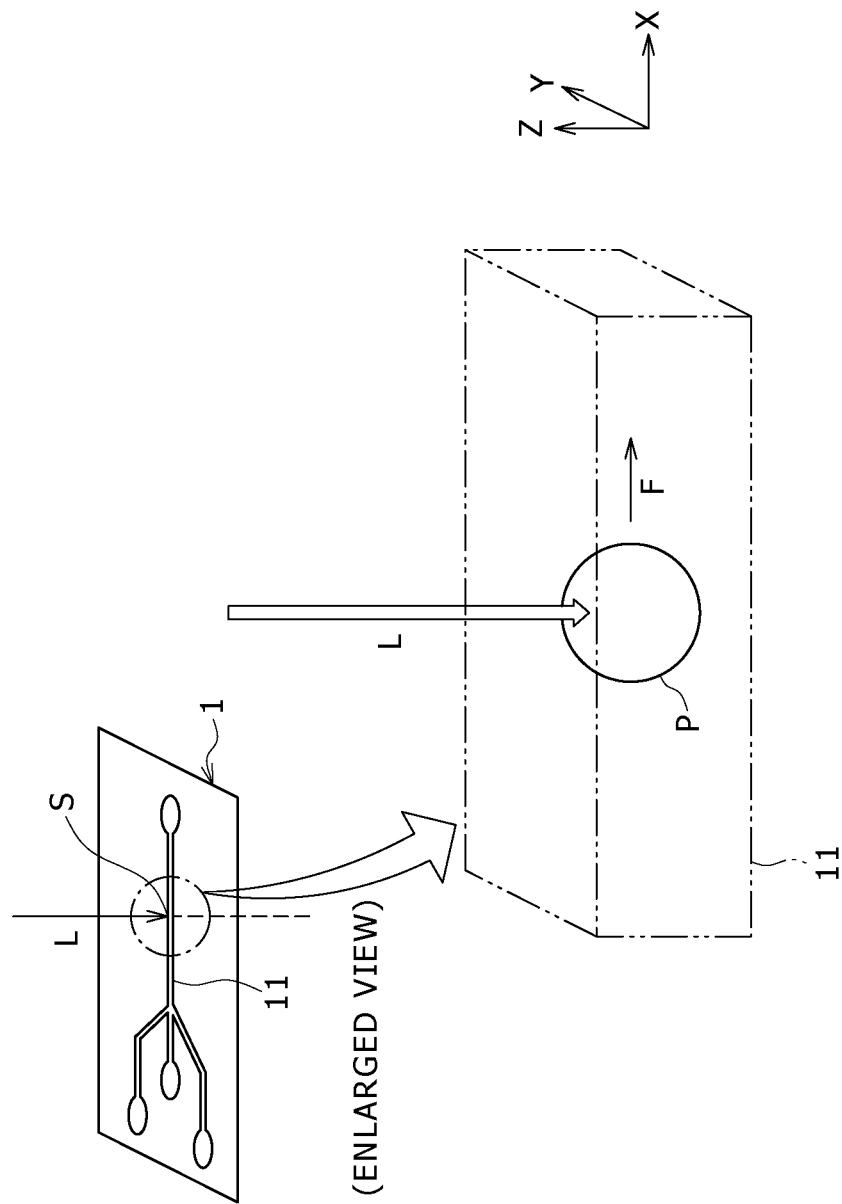
FIG. 2 is a diagram illustrating how the optical axis correcting means moves the relative position of the flow channel with respect to the laser beam.

The optical axis correcting unit moves the relative position of the flow channel 11 with respect to the laser beam by the method described below with reference to FIGS. 1 and 2. FIG. 2 is a schematic diagram showing the flow channel 11 near the illuminating site S in the microchip 1. There are shown in FIG. 2 the microparticle P, the solution flowing direction F (arrow), and the laser beam L (arrow).

The optical axis correcting unit moves either or both of the microchip 1 and the optical detecting units 21 and 22 in the incident direction (Z axis) of the laser beam L. In this way it adjusts the focus position of the laser beam L so that the laser beam L focuses on the microparticle P in the sample solution passing through the flow channel 11. Likewise, it also defocuses from the microparticle P.

Moreover, the optical axis correcting unit moves either or both of the microchip 1 and the optical detecting units 21 and 22 in the direction (Y axis) which is perpendicular to the plane (ZX plane) containing the incident direction of the laser beam L and the direction (X axis) in which the solution flows through the flow channel 11. In this way it adjusts the illuminating position of the laser beam L so that the laser spot coincides with the microparticle P in the sample solution passing through the flow channel 11. Likewise, it also shifts the laser spot from the microparticle P.

The optical axis correcting unit may be composed of a feed screw, guide, motor, etc., for example. It may be constructed in any way without specific restrictions so long as it is capable of moving the microchip 1 and/or the optical detecting units 21 and 22 along the Z axis and/or the Y axis. The optical axis correcting unit receives signals from the general control unit 3, according to which it moves the microchip 1 and/or the optical detecting units 21 and 22 along the Z axis and/or the Y axis so as to move the relative position of the flow channel 11 with respect to the laser beam.

(5) Acceleration Sensor and Temperature Sensor

There is shown in FIG. 1 the acceleration sensor 6 to detect vibration of the main body of the microparticle measuring apparatus. In addition, it sends signals to the general control unit 3 when it detects vibration.

There is shown in FIG. 1 the temperature sensor 5 to measure the temperature of the microchip 1. In addition, it sends signals to the general control unit 3 when it measures the temperature of the microchip 1 (especially the illuminating site S).

(6) General Control Unit

The general control unit 3 judges the optical characteristics of the microparticles under test in response to the electrical signals generated by the optical detecting unit 22 (for detection). It employs various parameters for judgment depending on the properties of the microparticles under test and the object of measurement. Such parameters include forward scattering light (which is useful for measurement of the size of the microparticles), side scattering light, Rayleigh scattering light, and Mie scattering light (which are useful for measurement of structure), and electrical signals converted from fluorescence. Analysis of such parameters is accomplished in the same way as in the existing flow cytometry. Incidentally, in the case where the characteristics of microparticles are examined electrically or magnetically, the parameters are electrical signals converted from changes in resistance, capacitance, inductance, impedance, and electric field between electrodes, or from changes in magnetization and magnetic field.

Also, the general control unit 3 sends signals to the optical axis correcting unit in response to the intensity of the electrical signals of reference microparticles which are issued from the optical detecting unit 22. Upon receipt of such signals, the optical axis correcting unit optimizes the relative position of the flow channel 11 with respect to the laser beam emitted from the optical detecting unit 21 (for illumination). In other words, it moves the microchip 1 and/or the optical detecting units 21 and 22 along the Z axis and/or Y axis so that the intensity of said electrical signals reaches a prescribed value.

Moreover, the general control unit 3 sends signals, in response to the detected signal sent from the acceleration sensor 6 and/or the measured value sent from the temperature sensor 5, to the valve 413 of the solution feeding unit 41 so that the calibration solution is fed to the sample solution inlet 121. Upon receipt of signals from the general control unit 3, the solution feeding unit 41 switches the valve 413 so that the calibration solution is fed to the sample solution inlet 121 for a prescribed period of time.

2. Action of the Microparticle Measuring Apparatus

Figure 3:
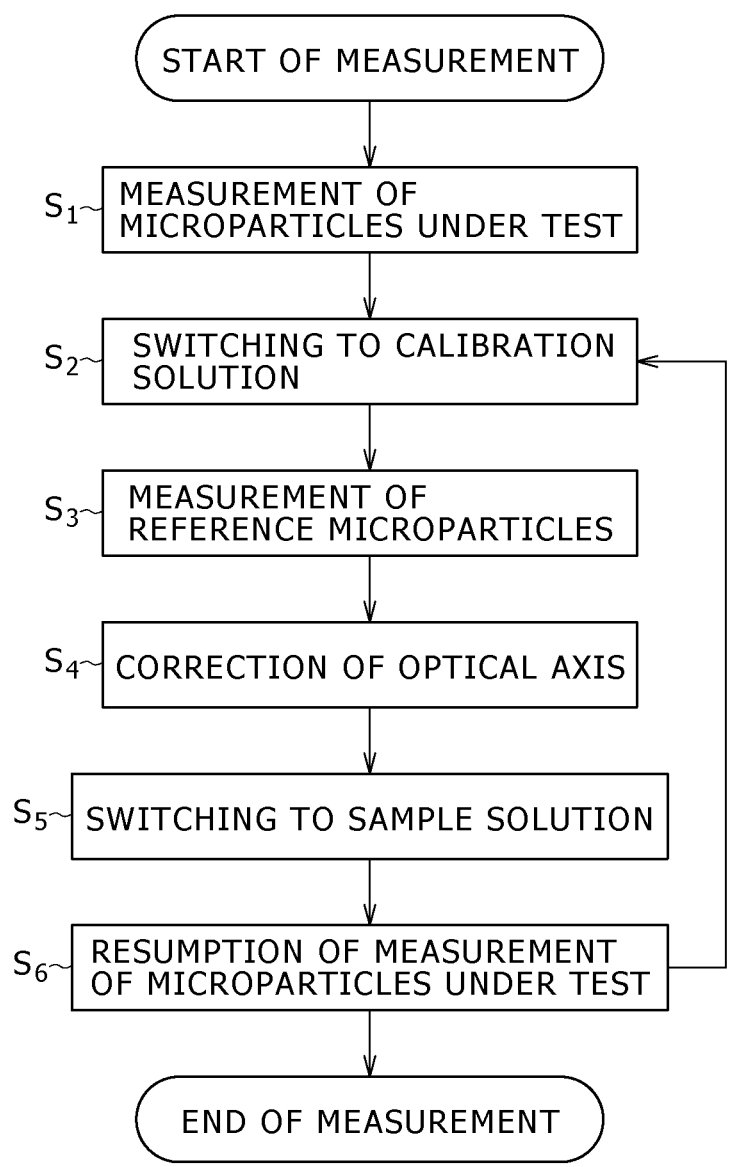
FIG. 3 is a flow chart illustrating the action of the microparticle measuring apparatus.

The action of the microparticle measuring apparatus will be described below with reference to FIG. 3. FIG. 3 is a flow chart illustrating the action of the microparticle measuring apparatus.

(1) Step $S_1$ (Measurement of Microparticles Under Test)

At the start of measurement, the solution feeding unit 41 feeds the sample solution so that the microparticles under test reach the illuminating site S of the flow channel 11. At the illuminating site S, the microparticles under test are examined for optical characteristics by the optical detecting units 21 and 22. The detected light is converted into electrical signals, which are subsequently sent to the general control unit 3. The general control unit 3 analyzes the electrical signals by using such parameters as scattered light and fluorescence and judges the optical characteristics of the microparticles. The results are stored.

(2) Step $S_2$ (Switching to Calibration Solution)

After the lapse of a prescribed length of time that followed the start of measurement of the microparticles under test, the general control unit 3 sends signals to the valve 413 of the solution feeding unit 41 to switch the valve 413 so that the supply of the sample solution from the solution feeding unit 41 is suspended and the supply of the calibration solution is started.

(3) Step $S_3$ (Measurement of Reference Microparticles)

After the supply of the calibration solution has started, the reference microparticles are sent to the illuminating site S of the flow channel 11 and they are examined there for optical characteristics by the optical detecting units 21 and 22. The calibration solution is fed for a prescribed period of time, during which the light detected from the reference microparticles is converted into electrical signals which are subsequently sent to the general control unit 3.

The reference microparticles should preferably be those microparticles which exhibit the same optical characteristics as the microparticles under test. For example, they may be incorporated with a fluorescent dye that produces the same intensity of fluorescence as the microparticles under test. Alternatively, they may have the same size as the microparticles under test so that they exhibit the same optical characteristics as the microparticles under test.

(4) Step $S_4$ (Correction of Optical Axis)

The general control unit 3 corrects the optical axis so as to optimize the relative position of the flow channel 11 with respect to the laser beam in response to the intensity of electrical signals of the reference microparticles. In other words, the general control unit 3 sends signals to the optical axis correcting unit so as to move the microchip 1 and/or the optical detecting units 21 and 22 along the Z axis and/or Y axis so that the intensity of said electrical signals attains a prescribed value. In this way the microparticle measuring apparatus corrects the displacement of the optical axis which has been caused during measurement by vibration, change in the pressure of the sheath flow, and the temperature change in the apparatus.

The following is a detailed description of how the microchip 1 and/or the optical detecting units 21 and 22 are moved along the Z axis and/or the Y axis so that the intensity of electrical signals of the reference microparticles attains the maximum value. For example, it is assumed that the mounting position of the microchip 1 has got out of position due to vibration and the position of the sample flow has moved in the direction of the Z axis shown in FIG. 2, thereby causing the focus of the laser beam L to get out of position. In this case, the general control unit 3 moves the microchip 1 oppositely in the direction of the Z axis so that the laser beam L focuses on the sample flow. Also, in the case where the microchip 1 is affected by temperature change due to irradiation with the laser beam L and the position of the sample flow moves in the direction of the Y axis, thereby causing the spot of the laser beam L to get out of position, the general control unit 3 moves the optical detecting units 21 and 22 in the negative direction of the Y axis so that the spot of the laser beam L coincides with the sample flow.

In this way it is possible to correct the displacement of the optical axis that has occurred during measurement, to detect highly efficiently the light for measurement emanating from the reference microparticles, and to maximize the electrical signals sent to the general control unit 3.

The relative position of the flow channel 11 with respect to the laser beam is optimized in such a way that the electrical signals of the reference microparticles which are sent to the general control unit 3 have the maximum intensity. Alternatively, it is optimized in such a way that the intensity of the electrical signals falls within a prescribed standard range. In the latter case, the optical axis correcting unit moves the microchip 1 and/or the optical detecting units 21 and 22 so that the focus and spot of the laser beam L coincide with the sample flow or gets out of position so that the intensity of electrical signals of the reference microparticles falls within the standard range.

Step $S_3$ (measurement of reference microparticles) and Step $S_4$ (correction of optical axis) may be carried out sequentially or simultaneously within a prescribed period of time after Step $S_2$ which starts the feeding of the calibration solution.

(5) Step $S_5$ (Switching to Sample Solution)

After the lapse of a prescribed length of time that followed the start of the feeding of the calibration solution, the general control unit 3 sends a signal to the valve 413 of the solution feeding unit 41 so as to suspend the feeding of the calibration solution from the solution feeding unit 41 and resumes the feeding of the sample solution.

(6) Step $S_6$ (Resumption of Measurement of Microparticles Under Test)

As soon as the feeding of the sample solution has resumed, the microparticles under test are fed again to the illuminating site S of the flow channel 11 and the microparticles under test are examined for optical characteristics by the optical detecting units 21 and 22.

In Step $S_4$ mentioned above, the relative position of the flow channel 11 with respect to the laser beam is optimized so that the electrical signals of the reference microparticles which are sent to the general control unit 3 have the maximum intensity. Therefore, the scattering light and fluorescence emanating from the microparticles under test can be detected highly efficiently for conversion into electrical signals.

When the relative position of the flow channel 11 with respect to the laser beam is optimized such that the electrical signal of reference microparticles which has been sent to the general control unit 3 has the maximum intensity, the intensity of electrical signal obtained from the microparticles under test in Step $S_6$ may occasionally deviate from the recognizable range (or dynamic range) of the general control unit 3.

The deviation of the intensity of electrical signal from the dynamic range is due to the fact that the ratio of amplification of the optical amplifier fluctuates under the influence of temperature change during measurement. One way of effectively avoiding such a situation is to optimize the relative position of the flow channel 11 with respect to the laser beam in such a way that the intensity of electrical signal of the reference microparticles falls within the previously established standard range. If the standard range is previously established according to the dynamic range of the general control unit 3 and the intensity of electrical signal of the reference microparticles is made to fall within this range, the scattered light and fluorescence emanating from the microparticles under test can be converted into an electrical signal having an intensity within the recognizable range.

Moreover, Step $S_4$ may be carried out in such a way that the ratio of amplification of the optical amplifier is given feedback or the analysis parameter in the general control unit 3 is given feedback so that the electrical signal of reference particles which is sent to the general control unit 3 may possibly be converted into the intensity that falls within the standard range. In this case, if Step $S_4$ employs as the reference microparticles some kind of particles which exhibit the same optical characteristics as the microparticles under test, it will be possible to achieve an efficient feedback to the amplification of the optical amplifier and the analysis parameter.

After the elapse of a prescribed length of time that followed the resumption of measurement of the microparticles under test, the general control unit 3 sends a signal again to the valve 413 of the solution feeding unit 41 so as to suspend the feeding of the sample solution from the solution feeding unit 41 and start the feeding of the calibration solution, and repeat Step $S_2$. Subsequently, Steps $S_3$ to $S_6$ are repeated until measurement is completed.

As mentioned above, the microparticle measuring apparatus repeats Steps $S_2$ to $S_6$, thereby to optimize the relative position of the flow channel 11 with respect to the laser beam while the sample solution is being fed subsequently in response to the intensity of electrical signals from the reference microparticles at the time of the feeding of the sample solution. Thus, even though the optical axis gets out of position due to vibration and change in pressure and temperature during measurement, the microparticle measuring apparatus is capable of automatically correcting such displacement and performing highly accurate measurement.

(7) Timing of Step $S_2$

The foregoing description is concerned with the case in which the feeding of the calibration solution and the feeding of the sample solution are switched at certain intervals and the step for the optical axis correction in Step $S_4$ is carried out at certain intervals. The construction of the microparticle measuring apparatus may be modified such that Step $S_4$ for the optical axis correction is carried out not only automatically at certain intervals but also manually by the operator who switches the sample solution and the calibration solution at any time according to need.

In addition, the construction of the microparticle measuring apparatus may be modified such that the sample solution and the calibration solution are switched automatically in response to the detection signal sent from the acceleration sensor 6 and/or the measured value sent from the temperature sensor 5. The acceleration sensor 6 detects vibration of the apparatus proper and sends the thus detected signal to the general control unit 3. In response to this signal, the apparatus switches to the calibration solution and corrects the optical axis in Step $S_4$, so that it rapidly corrects the displacement of the optical axis due to vibration and carries out measurement.

Also, the temperature sensor 5 measures the temperature of the microchip 1 (particularly the temperature of the illuminating site S) and sends the measured value to the general control unit 3. When the measured value exceeds a prescribed value, the apparatus switches to the calibration solution and corrects the optical axis in Step $S_4$, so that is corrects the displacement of the optical axis due to temperature change from time to time and carries out measurement.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microparticle measuring apparatus comprising:
a flow channel through which a solution containing microparticles flows;
optical detecting means for directing a laser beam to microparticles passing through said flow channel and detecting light for measurement emanating from said microparticles and converting the thus detected light into electrical signals;
solution feeding means for feeding said flow channel with either a sample solution containing microparticles of interest or a calibration solution containing reference microparticles that exhibit uniform optical characteristics;
a control means to instruct the solution feeding means that the calibration solution is to flow through the flow channel after determining that the relative position of said flow channel with respect to said laser beam should be optimized; and
optical axis correcting means for optimizing the relative position of said flow channel with respect to said laser beam in response to the intensity of electrical signals from said reference microparticles.

2. The microparticle measuring apparatus as defined in claim 1, wherein said optical axis correcting means moves said relative position so that the intensity of electrical signals from said reference microparticles reaches a prescribed value.

3. The microparticle measuring apparatus as defined in claim 2, wherein said optical axis correcting means moves said relative position in the incident direction of said laser beam and/or in the direction perpendicular to the plane containing said direction and the flowing direction of said flow channel.

4. The microparticle measuring apparatus as defined in claim 3, wherein said solution feeding means feeds said flow channel with either said sample solution or said calibration solution alternately, and
said optical axis correcting means optimizes said relative position while said sample solution is flowing to said flow channel in response to the intensity of electrical signals from said reference microparticles which was previously measured while said calibration solution was flowing to said flow channel.

5. The microparticle measuring apparatus as defined in claim 4, further comprising an acceleration sensor to detect vibration of the apparatus proper and in which said control means causes said calibration solution to feed through said flow channel for a prescribed period of time in response to receiving the output of detected signals from said acceleration sensor.

6. The microparticle measuring apparatus as defined in claim 1, in which said flow channel is formed on a microchip and which has a temperature sensor to measure the temperature of said microchip and said control means causes said calibration solution to feed through said flow channel for a prescribed period of time when the value measured by said temperature sensor exceeds a prescribed value.

7. The microparticle measuring apparatus as defined in claim 1, wherein said control means selects the calibration solution to flow through the flow channel after a lapse of a predetermined length of time during which the sample solution flowed through the flow channel.

* * * * *